United States Patent
Huffman

(10) Patent No.: US 6,255,550 B1
(45) Date of Patent: Jul. 3, 2001

(54) STABILIZATION OF THE REAGENT DIMETHYL TITANOCENE

(75) Inventor: Mark Huffman, Edgewater, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/428,316

(22) Filed: Oct. 28, 1999

Related U.S. Application Data

(60) Provisional application No. 60/105,954, filed on Oct. 28, 1998.

(51) Int. Cl.$^7$ ............... C07C 1/00; C07C 1/20; C07D 265/00
(52) U.S. Cl. ............ 585/638; 585/639; 544/106; 544/154; 544/170; 544/178
(58) Field of Search .................. 585/638, 639; 502/152, 349; 556/53; 544/106, 154, 170, 178

(56) References Cited

U.S. PATENT DOCUMENTS

| | | |
|---|---|---|
| 2,992,212 | 7/1961 | De Butts et al. . |
| 3,104,249 | 9/1963 | Clauss et al. . |
| 3,453,241 * | 7/1969 | Jeurissen et al. .............. 556/53 |
| 5,087,790 | 2/1992 | Petasis et al. . |
| 5,169,905 | 12/1992 | Hashiguchi et al. . |
| 5,474,716 | 12/1995 | Lisowsky . |
| 5,523,435 | 6/1996 | Lisowsky . |
| 5,569,746 | 10/1996 | Lee et al. . |
| 5,637,699 | 6/1997 | Dorn et al. . |
| 5,892,082 * | 4/1999 | Cai et al. .................. 556/53 |
| 6,063,950 * | 5/2000 | Huffman et al. .............. 556/53 |

FOREIGN PATENT DOCUMENTS

| | | |
|---|---|---|
| 1 037 446 | 4/1956 | (DE) . |
| 0 704 764 * | 4/1996 | (EP) . |

OTHER PUBLICATIONS

Chenault, H.K., et al, *Org. Chem.*, vol. 59, p. 6167 (1994).
Claus, K., et al, *Ann Der Chemie*, vol. 654:8(1962).
Deshong, P., et al. *J. Org. Chem.*, vol. 56, p. 3207(1991).
Erskine, G.J., et al, *Organomet, Chem.*, vol. 170 p. 51(1979).
Glivicky, A., et al, *Can. J. Chem.*, vol. 51:2609(1973).
Kuzmich, D., et al, *J. Am. Chem. Soc.*, vol. 116, p. 6943 (1994).
Nifant'Ev, I.E., et al, *J. Of Organometal. Chem.*, vol. 435, Nos. 1–2, pp. 37–42.
Payack, J.F., et al, *New J. Of Org. Syn.*, vol. 27, No. 6, pp. 707–709(1995).
Petasis, N.A., et al, *J. Am. Chem. Soc.*, vol. 112, pp. 6392–6394(1990).
Petasis, N.A., et al, *Tetrahedron Lett.*, vol. 31, p. 6799(1990).
Petasis, N.A., et al, *J. Am. Chem. Soc.*, vol. 115, p. 7208(1993).
Petasis, N.A., et al, *Tetrahedron Lett.*, vol. 33, p. 1721(1993).
Petasis, N.A., et al, *Tetrahedron Lett.*, vol. 36, p. 2393(1995).
Piper, T.S., et al, *J. Inorg. Nucl. Chem.*, vol. 3, pp. 104–124 (1956).
Razuvaev., G.A., et al, *Doklady Akad, Nauk, SSR*, vol. 189, p. 884–885(1996).
Scholz, J., et al, *Chem. Ber.*, vol. 120, p. 1369(1987).
Swenton, J.S., et al, *J. Org. Chem.*, vol. 56, p. 6156(1991).

* cited by examiner

Primary Examiner—Walter D. Griffin
(74) Attorney, Agent, or Firm—J. Eric Thies; David L. Rose

(57) ABSTRACT

The present invention is directed to organic solutions of the reagent dimethyl titanocene which further comprise a sterically hindered ester and optionally titanocene dichloride. Stability of the reagent dimethyl titanocene is enhanced by the presence of the sterically hindered ester.

18 Claims, No Drawings

STABILIZATION OF THE REAGENT DIMETHYL TITANOCENE

This application claims priority from U.S. Ser. No. 60/105,954, filed Oct. 28, 1998.

Dimethyl titanocene is an effective methylenating reagent for a variety of carbonyl compounds, including esters and lactones (N. A. Petasis and E. I. Bzowej, *J. Am. Chem. Soc.*, 112, 6392–6394 (1990); U.S. Pat. No. 5,087, 790). It is well recognized in the art that dimethyl titanocene has become a valuable synthetic tool. The use of dimethyl titanocene has been extensive, see e.g. N. A. Petasis and M. A. Patane, *Tetrahedron Lett.*, 31, 6799 (1990); P. DeShong and P. J. Rybczynski, *J. Org. Chem.*, 56, 3207 (1991); J. S. Swenton, D. Bradin, B. D. Gates, *J. Org. Chem.*, 56, 6156 (1991); N. A. Petasis and E. I. Bzowej, *Tetrahedron Lett.*, 34, 1721 (1993); H. K. Chenault and L. F. Chafin, *J. Org. Chem.*, 59, 6167 (1994); D. Kuzmich, S. C. Wu, D. -C. Ha, C. -S. Lee, S. Ramesh, S. Atarashi, J. -K. Choi and D. J. Hart, *J. Am. Chem. Soc.*, 116, 6943 (1994). The preparation of dimethyl titanocene is disclosed in PCT Patent Publication WO 97/09336 and U.S. Pat. No. 5,892,082.

Synthetic methodology may require the availablity of dimethyl titanocene on a multi-kilogram scale, however, it has been noted that dimethyl titanocene is unstable in the solid phase and evaporation of solutions containing the reagent have decomposed unpredictably (for a discussion of the solid state stability of dimethyl titanocene see: G. J. Erskine, J. Hartgerink, E. L. Weinberg and J. D. McCowan *J. Organomet. Chem.*, 170, 51 (1979) and references cited therein). Accordingly, it is hazardous to handle on a large scale. In addition, when methylenating esters or lactones dimethyl titanocene may react with the product vinyl ether, thereby reducing the yield.

Accordingly, there is a need in the art for methodology to enhance the safety and improve the efficiency of dimethyl titanocene. The present invention provides a safer and more efficient method for storing solutions of dimethyl titanocene and conducting reactions with the reagent dimethyl titanocene.

SUMMARY OF THE INVENTION

The present invention is directed to the use of a sterically hindered ester to stabilize the reagent dimethyl titanocene ($CP_2Ti(CH_3)_2$). In an alternate embodiment, the present invention is directed to a solution of dimethyl titanocene ($CP_2Ti(CH_3)_2$) which comprises an organic solvent and which further comprises a sterically hindered ester and optionally titanocene dichloride. Stability of the reagent dimethyl titanocene is enhanced by the presence of the sterically hindered ester.

DETAILED DESCRIPTION OF THE INVENTION

The present invention is directed to the use of a sterically hindered ester to stabilize the reagent dimethyl titanocene ($CP_2Ti(CH_3)_2$). In an alternate embodiment, the present invention is directed to a solution of dimethyl titanocene ($CP_2Ti(CH_3)_2$) in an organic solvent which further comprises a sterically hindered ester and optionally titanocene dichloride.

In one embodiment, the present invention is directed to a process for the conversion of a starting material containing a carbon-oxygen double bond to a corresponding product containing a carbon-carbon double bond which comprises: reacting the compound with dimethyl titanocene in a reaction mixture which comprises an organic solvent and a sterically hindered ester, whereby the carbon-oxygen double is replaced by a carbon-carbon double bond to provide an olefin.

In the present invention it is preferred that the starting compound containing a carbon-oxygen double bond is selected from the group consisting of aldehydes, ketones, esters, lactones, amides and lactams.

In the present invention it is preferred that at least one equivalent of dimethyl titanocene is employed. In the present invention it is more preferred that at least two equivalents of dimethyl titanocene are employed.

In the present invention it is preferred that titanocene dichloride and/or chloromethyl titanocene is present in the solution.

In an alternate embodiment, the process further comprises recovery of the product olefin from the reaction mixture.

In an alternate embodiment, the process further comprises reacting of the product olefin in situ prior to recovery from the reaction mixture. Such reacting may comprise catalytic hydrogenation or hydroboration.

In the present invention it is preferred that the sterically hindered ester be of the formula:

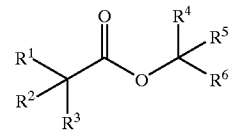

wherein:
$R^1$ and $R^4$ are hydrogen;
$R^2$ and $R^3$ are independently selected from the group consisting of:
  (1) $C_{1-8}$ alkyl, wherein the alkyl is unsubstituted or substituted with $C_{1-6}$ alkyl, $C_{5-8}$ cycloalkyl or phenyl, and wherein $R^2$ and $R^3$ may be joined together to form a $C_{5-8}$ cycloalkyl ring,
  (2) $C_{5-8}$ cycloalkyl, and
  (3) phenyl;
$R^5$ and $R^6$ are independently selected from the group consisting of:
  (1) $C_{1-8}$ alkyl, wherein the alkyl is unsubstituted or substituted with $C_{1-6}$ alkyl, $C_{5-8}$ cycloalkyl or phenyl, and wherein $R^5$ and $R^6$ may be joined together to form a $C_{5-8}$ cycloalkyl ring,
  (2) $C_{5-8}$ cycloalkyl, and
  (3) phenyl;
or
$R^1$, $R^2$ and $R^3$ are hydrogen and $R^4$, $R^5$ and $R^6$ are independently selected from the group consisting of:
  (1) $C_{1-8}$ alkyl, wherein the alkyl is unsubstituted or substituted with $C_{1-6}$ alkyl, $C_{5-8}$ cycloalkyl, phenyl, and wherein two of $R^4$, $R^5$ and $R^6$ may be joined together to form a $C_{5-8}$ cycloalkyl ring,
  (2) $C_{5-8}$ cycloalkyl, and
  (3) phenyl.

In the sterically hindered ester it is preferred that:
$R^1$, $R^2$ and $R^3$ are hydrogen;
$R^4$ and $R^5$ are methyl; and
$R^6$ is selected from: methyl, ethyl, propyl, benzyl and cyclohexylmethyl.

In the sterically hindered ester it is also preferred that:
$R^1$ and $R^4$ are hydrogen;
$R^2$ and $R^3$ are methyl; and
$R^5$ and $R^6$ are independently selected from: methyl, ethyl, propyl, or $R^5$ and $R^6$ are joined together to form cyclohexyl.

In a preferred embodiment, the sterically hindered ester is selected from the group consisting of: t-butyl acetate; 1,1-dimethyl-2-phenylethyl acetate; 1,1-dimethyl-3-phenylpropyl acetate; dihydroterpinyl acetate; isopropyl cyclohexane carboxylate; isopropyl isobutyrate; methyl pivalate; ethyl acetate; and isobutyl acetate.

In a more preferred embodiment, the sterically hindered ester is selected from the group consisting of: 1,1-dimethyl-2-phenylethyl acetate; and t-butyl acetate.

In an even more preferred embodiment, the sterically hindered ester is 1,1-dimethyl-2-phenylethyl acetate.

It will be appreciated by one skilled in the art that the sterically hindered ester which is employed to stabilize the dimethyl titanocene is present in addition to any substrate carbonyl compound which may be present. It will be further appreciated by one skilled in the art that the appropriate sterically hindered ester will meet two requirements: (1) its rate of reaction with the reagent dimethyl titanocene will be slower than the rate of reaction of the substrate carbonyl compound with the reagent dimethyl titanocene; and (2) its rate of reaction with the reagent dimethyl titanocene will be faster than the rate of reaction of the product vinyl compound with the reagent dimethyl titanocene, thereby expending any excess dimethyl titanocene which may be present. The relative rate of reaction of the sterically hindered ester may be readily determined by one skilled in the art through routine experimentation.

In a preferred embodiment, dimethyl titanocene is prepared from the reaction of titanocene dichloride with slightly more than two equivalents of methylmagnesium chloride. The reaction is exothermic and should be maintained below 5° C. to avoid decomposition. The reaction mixture is quenched into an aqueous mixture below 5° C., and the quenched mixture is filtered to avoid emulsions in the phase separation and water wash. The wet dilute dimethyltitanocene solution is vacuum distilled to azeotropically dry and to reach the desired reaction volume. The potential instability of dimethyltitanocene requires some special consideration. Unstabilized solutions of dimethyl titanocene can undergo rapid exothermic decomposition, generating methane gas, initiating at temperatures as low as 40° C. In the presence of an ester, this runaway decomposition is replaced by a slow controlled reaction which converts the ester to a vinyl ether and the dimethyltitanocene to an oxo species. Ester stabilization is required both for reagent storage and for the vacuum distillation in order to minimize hazards resulting from an inadvertent warm-up. In a preferred embodiment, the sterically hindered ester 1,1-dimethyl-2-phenylethyl acetate is employed at 30 mol % vs. dimethyltitanocene and is further accompanied by a small amount of $Cp_2TiCl_2$ (or $Cp_2TiClMe$, which results from ligand exchange with dimethyl titanocene). This sterically hindered ester reacts slowly enough that it does not interfere with subsequent use of the reagent dimethyl titanocene, thus it is well suited for stabilization of dimethyl titanocene during storage. In a preferred embodiment where dimethyl titanocene is stabilized with 1,1-dimethyl-2-phenylethyl acetate, additional titanocene dichloride cannot be added until after azeotropic drying or it will speed the decomposition of the dimethyltitanocene due to reaction with water. In this embodiment, an additional, more reactive ester must be used for stabilization during azeotropic drying. Ethyl acetate is a representative more reactive ester which may be used for this purpose. Because even small amounts of ethyl acetate will interfere with use of dimethyl titanocene as a reagent, however, after the solution is dry, the titanocene dichloride is added and the ethyl acetate is removed by further vacuum distillation in the presence of 1,1-dimethyl-2-phenylethyl acetate.

In a preferred embodiment, selective olefination of a starting compound which contains multiple carbon-oxygen double bonds is carried out by varying the equivalents of sterically hindered ester.

In a preferred alternate embodiment, the present invention is directed to a process for the preparation of (2R-cis)-2-[[1-[3.,-bis(trifluoromethyl)phenyl]-ethenyl]oxy]-3-(4-fluorophenyl)-4-(phenylmethyl)-mopholine which comprises:

reacting (2R-cis)-3,5-bis(trifluoromethyl)-benzeneacetic acid 3-(4-fluorophenyl)-4-(phenylmethyl)-2-morpholinyl ester with dimethyl titanocene in an organic solvent in the presence of a sterically hindered ester and optionally titanocene dichloride.

This reaction may be depicted as follows:

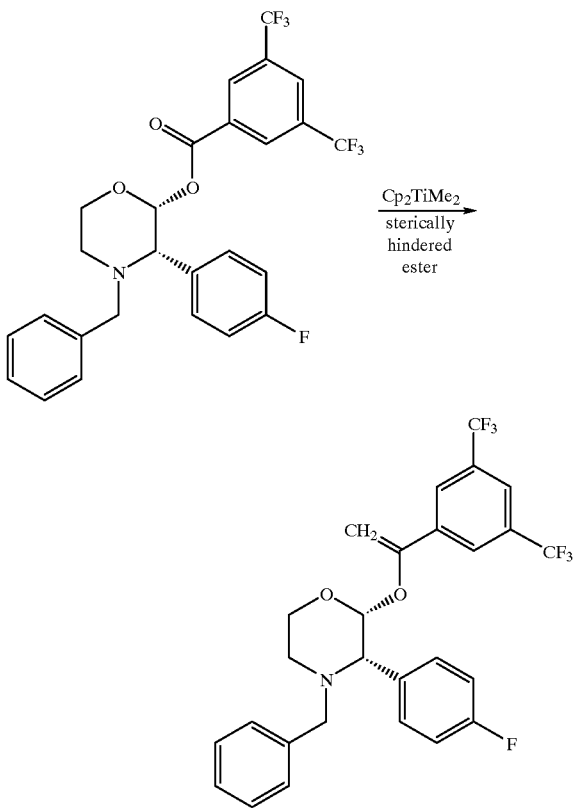

A suitable temperature for this reaction is in the range of about 30–100° C., preferably about 60–90° C., and most preferably about 80° C.

In the present invention the organic solvent may be selected from the group consisting of: toluene; xylene (including o-xylene, m-xylene, p-xylene, and mixtures thereof); benzene; petroleum ether; hexane; heptane; cumene; mesitylene; diethyl ether; tetrahydrofuran; digylme (2-methoxy-ethyl ether); methyl-t-butyl ether; a chlorinated hydrocarbon such as dichloromethane, chloroform, carbon tetrachloride, dichloroethane, chlorobenzene, ortho-dichlorobenzene; and the like; and mixtures thereof. In a preferred embodiment, the organic solvent comprises a solvent selected from toluene, xylene and benzene, and which may additionally comprise tetrahydrofuran. In a more preferred embodiment, the organic solvent comprises a solvent which is toluene, and which may additionally comprise tetrahydrofuran. Other ingredients may be present in the reaction mixture, for example, to facilite the preparation of the product or to monitor the progress of the reaction.

"Dimethyl titanocene" is represented by the formula $Cp_2Ti(CH_3)_2$ or $Cp_2TiMe_2$, wherein "Cp" indicates the presence of a cyclopenta-dienyl (cyclopentadienylide) ("$C_5H_5$") group. In particular, dimethyl titanocene has the following chemical structure:

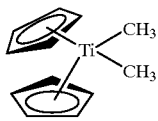

"Titanocene dichloride" is represented by the formula $Cp_2TiCl_2$.

The preparation of the desired compound with the process of the present invention may be carried out in sequential or convergent synthetic routes. It is noted that in some cases the order of carrying out the subject reactions may be varied to facilitate the reaction or to avoid unwanted reaction products. In general, the process of the present invention is conducted in a sequential manner as presented herein.

NMR spectra were run in $CDCl_3$ and the $^1H$ and $^{13}C$ spectra were measured at 250 and 62.9 MHz. The proton spectra were run with a 10 s delay between pulses for the wt % assay. Toluene was dried to less than 150 µg/mL water (by Karl Fisher titration) with 3 Å sieves. Standard inert atmosphere techniques were used for the reaction and work-up.

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

EXAMPLE 1

Dimethyltitanocene

| Material | Amount |
| --- | --- |
| Titanocene dichloride (248.98) | 254.5 g, 1.022 mol (249 g + 5.48 g) |
| MeMgCl (3.0M in THF) | 700 mL, 2.10 mol |
| Tetrahydrofuran (THF) | 772 mL |
| Toluene | 3750 mL (1120 + 2630) |
| Ethyl Acetate | 560 mL |
| $NH_4Cl$ | 27.0 g |
| Celite | 62.3 g |
| Water | 1873 mL (877 mL + 996 mL) |
| 1,1-dimethyl-2-phenylethyl acetate (192.26) | 50.8 g, 264 mmol |

The water content of THF is determined (max. 200 µg/mL). Titanocene dichloride (249 g, 1.0 mol) is slurried in THF (772 mL) under nitrogen. The suspension is maintained below 5° C. with a −10° C. bath while MeMgCl (700 mL of 3.0 M in THF, 2.10 mol) is added over 60 min. The slurry becomes thick with $MgCl_2$; strong stirring is required. The mixture is stirred another 30 min at 0 to 5° C., then the reaction supernatant is assayed for completion by HPLC (maximum concentration of chloromethyltitanocene 2.5 mg/mL) or $^1H$ NMR (max. 2% vs. $Cp_2TiCl_2$). In a second flask, a quench mixture is prepared from 3 wt % $NH_4Cl$ in water (27.0 g in 877 mL), toluene (1120 mL), and Celite (62.3 g). The quench mixture is rapidly stirred below 5° C. while the reaction mixture is slowly transferred into it using teflon tubing as a cannula.

The three-phase mixture is filtered, rinsing with ethyl acetate (560 mL). The filtrate is transferred into a separatory funnel and the aqueous layer cut away. The red organic layer is washed once with water (996 mL) cutting away any interfacial emulsion with the aqueous. (Note: careful exclusion of air is not required for filtration and extraction on small scale.) The final organic layer is assayed for dimethyltitanocene concentration by titration or $^1H$ NMR (typical 7.2 wt %).

A quantity of 1,1-dimethyl-2-phenylethyl acetate (DMPEA) is charged equal to 0.30 mol eq. relative to dimethyltitanocene (typical 50.8 g, 264 mmol). The wet solution is concentrated by vacuum distillation to a volume of 1170 mL (max temp 35° C.). Note: Vacuum concentration azeotropically removes water; this operation should be started without delay as the reagent is less stable in the presence of water.

The now dry solution is treated with titanocene dichloride (5.48 g, 22 mmol) and stirred 30 min while the solid dissolves. Vacuum distillation continues while toluene is fed into the batch, maintaining the volume at ≧995 mL. Distillation continues until ethyl acetate is removed to a level below 0.01 eq. vs dimethyl-titanocene (0.08% of batch by weight) and the final batch volume is 995 mL (ca. 2630 mL toluene added). Dimethyltitanocene concentration is measured by titration or $^1H$ NMR (target 20 wt %). The reagent is stored under nitrogen at ≦5° C. protected from light. Note: For safety, the amount of ethyl acetate should not be allowed to drop below 1.0 eq. vs. $Cp_2TiMe_2$ (ca. 8% of batch by weight) until after $Cp_2TiCl_2$ is charged. Note: Pressure will slowly develop upon storage from the formation of methane gas so suitable containers should be used.

HPLC method:

| | |
| --- | --- |
| Column | Zorbax CN column (25 cm × 4.6 mm × 5 µm particles) with Zorbax CN guard column |
| Mobile phase | 70% HPLC grade hexanes/30% THF (with BHT) (v/v) |
| Gradient | isocratic |
| Flow rate | 1.0 mL/min |
| Temperature | 25° C. |
| Detection | 254 nm |
| Injection volume | 20 µL |
| Sample diluent | 70% HPLC grade hexanes/30% THF (with BHT) (v/v) |

Amber glass vials and volumetrics are used for samples. The mobile phase is thoroughly degassed and stored in amber bottles to prevent formation of peroxide which can interfere with the method. Monochloro monomethyl titanocene ($Cp_2TiMeCl$) is unstable and must be quantitated via a titanocene dichloride ($Cp_2TiCl_2$) reference standard. The relative response factor of monochloro monomethyltitanocene/titanocene dichloride is 1.1.

Typical Retention Times:
toluene: 3.2 min (not integrated)
Dimethyltitanocene, $Cp_2TiMe_2$: 3.7 min
Dimer, $(Cp_2TiMe)_2O$: 4.6 min
Chloromethyl titanocene, $Cp_2TiMeCl$: 4.9 min
Titanocene dichloride, $Cp_2TiCl_2$: 8.3 min Titration Assay:

Pipet 10 mL of toluene and 10 mL of 0.2 N standardized iodine in toluene into a 150 mL beaker containing a magnetic stirrer and tare it on an analytical balance. Accurately add 200 mg sample to the beaker dropwise, stir for 1 minute, then add 50 mL of aqueous KI solution (concentration=120 mg/mL) and 10 mL of DI water. The unreacted iodine in solution is back-titrated with standardized 0.1N aqueous $Na_2S_2O_3$ solution to a single endpoint.

$^1$H NMR Analysis:

An aliquot of 0.075 mL of dimethyltitanocene solution (supernatant for end of MeMgCl addition sample) is transferred into 0.6 mL of $CDCl_3$ (stored over $K_2CO_3$ to remove HCl). Acquisition of $^1$H NMR spectrum incorporates a 10 second relaxation delay. For end of reaction, integrate $Cp_2TiMeCl$ signal (6.3 ppm) vs. $Cp_2TiMe_2$ (6.1 ppm). For final concentration, integrate Cp signal (6.1 ppm, 10 H) against the toluene $CH_3$ group (2.5 ppm, 3 H) and DMPEA $CH_3$ (1.5 ppm, 6 H).

EXAMPLE 2

Dimethyltitanocene

| Material | Amount |
| --- | --- |
| Titanocene dichloride (248.98) | 1.39 kg, 5.58 mol, 1 eq. |
| Toluene (d 0.865) | 15.3 L, 13.2 kg |
| MeMgCl (3.0M, THF) | 4.19 L, 12.6 mol, 2.25 eq. |
| 12% $NH_4Cl$ in water | 4.14 kg (3.67 L water + 0.47 kg $NH_4Cl$) |
| water washes | 3 × 3.20 L |

Titanocene dichloride ($Cp_2TiCl_2$) is slurried in toluene (KF<200 μg/mL) under nitrogen. (If not crystalline, the $Cp_2TiCl_2$ is broken up by rapid stirring for a few hours.) The suspension is cooled below 0° C., and the MeMgCl solution is added over ~1 h, maintaining the internal temperature below 5° C. After the addition is complete, the batch is stirred at 0–5° C. for 1 to 2 h, while the remaining red solid $Cp_2TiCl_2$ is consumed.

The reaction mixture is slowly quenched into a stirring cold aqueous 12% solution of $NH_4Cl$, maintaining a temperature of 0–5° C. The mixture is warned to 15–20° C. and the phases allowed to separate. The aqueous layer is removed, and the organic layer is washed with water three times.

A portion of (2R-cis)-3,5-bis(trifluoromethyl)-benzeneacetic acid 3-(4-fluorophenyl)-4-(phenylmethyl)-2-morpholinyl ester is added to the final organic solution (749 g, 1.42 mol, ca. 30 mol % vs. $Cp_2TiMe_2$). The solution is vacuum concentrated (maximum internal temperature 25° C.) to a target of 5.98 kg, ca. 6.5 L. (Caution: Heating solutions of $Cp_2TiMe_2$ without the ester present can lead to violent decomposition. Allowing a solution of $Cp_2TiMe_2$ to evaporate to dryness can lead to violent decomposition.)

The solution is checked by $^1$H NMR integration. NMR method: 0.075 mL of solution is transferred into 0.5 mL of $CDCl_3$. Acquisition of $^1$H NMR spectrum incorporates a 10 second relaxation delay. Integrate the Cp signal (6.1 ppm, 10 H) against the toluene $CH_3$ group (2.5 ppm). $Cp_2TiMe_2$ should be 20 wt % (excluding ester). Range is 18–22%. Solution can be stored below 0° C. for a short time before olefination reaction.

EXAMPLE 3

(2R-cis)-2-[[1-[3.5-bis(Trifluoromethyl)phenyl]ethenyl]oxy]-3-(4-fluorophenyl)-4-(phenylmethyl)mopholine

| Material | Amount |
| --- | --- |
| (2R-cis)-3,5-bis(trifluoromethyl)-benzeneacetic acid 3-(4-fluorophenyl)-4-(phenylmethyl)-2-morpholinyl ester (527.44) | 1.00 kg, 1.90 mol, 1 eq. |
| dimethyltitanocene (208.14) | 0.99 kg, 4.74 mol, 2.5 eq., as 20 wt % in toluene |
| 1,1-dimethyl-2-phenylethyl acetate (196.26) | 0.28 kg, 1.42 mol, 0.75 eq |
| titanocene dichloride (248.98) | 0.030 kg, 0.12 mol, |
| heptane | 5.7 L + rinse (1.9 L) |
| sodium bicarbonate | 0.25 kg, 2.98 mol |
| ethanol (d; 0.785) | 2.2 L, 1.7 kg |
| water | 0.20 L, 0.20 kg |
| toluene (d; 0.865) | 1.3 L wash, |
| n-propanol (d; 0.804) | 32 L |
| water | 8.69 L |

The dimethyltitanocene solution (20 wt % in toluene) is combined with (2R-cis)-3,5-bis(trifluoromethyl)-benzeneacetic acid 3-(4-fluorophenyl)-4-(phenylmethyl)-2-morpholinyl ester, 1,1-dimethyl-2-phenylethyl acetate, and titanocene dichloride. The mixture is vacuum degassed, then stirred under nitrogen and heated to 80° C.; gas evolution (methane) occurs. After 5.5 h, the reaction is assayed by HPLC. [HPLC: Column=Inertsil phenyl 4.6×250 mm; Mobile phase=80/20-$CH_3CN$/water; Flow rate=1.5 mL/min; Temperature=20° C.; Detection=220 nm; Sample makeup= $CH_3CN$. Retention times: toluene 2.6 min; dimethylphenylethyl acetate 2.7 min; $Cp_2TiMe_2$ 3.4 min (broad); (2R-cis)-3,5-bis(trifluoromethyl)-benzeneacetic acid 3-(4-fluorophenyl)-4-(phenylmethyl)-2-morpholinyl ester: 4.3 min; (2R-cis)-2-[[1-[3.5-bis(Trifluoromethyl)phenyl]ethenyl]oxy]-3-(4-fluorophenyl)-4-(phenylmethyl) mopholine: 5.0 min; $(Cp_2TiMe)_2O$: 5.3 min.]

Heating at 80° C. continues until the cis-ester integration is less than 0.5 % that of the vinyl ether. The mixture is cooled to 25° C. over 1 h, while $(Cp_2TiMe)_2O$ crystallizes.

The slurry is vacuum concentrated (25–30 torr, max temp 30° C.) to a volume of 3.6 L. Vinyl ether concentration in the supernatant should be 31–34 wt %. The suspension is stirred at 20° C. and heptane (5.7 L) is added over 30 min. Vinyl ether concentration in the supernatant should be 14.5%, $(Cp_2TiMe)_2O$ ca. 1.7 wt %.

The mixture is filtered, rinsing with heptane (1.9 L). Solid $(Cp_2TiMe)_2O$ is dried under vacuum at 20° C., protected from light. The filtrate is concentrated under vacuum (max temp 30° C.) to a volume of 4.4 L (vinyl ether concentration ca. 27.5 wt %). $NaHCO_3$ (0.25 kg) is added first. With stirring, ethanol (2.2 L) and then water (0.2 L) are added next, causing slow gas evolution. The mixture is stirred at 60° C. under a reflux condenser for 5 h., then cooled to 20° C. HPLC confirms the consumption of $Cp_2TiMe_2$ and $(Cp_2TiMe)_2O$. The mixture is filtered, rinsing with toluene (1.3 L).

The filtrate is vacuum concentrated (45–50° C.), and switched to n-propanol (volume 9.66 L, vinyl ether concentration 100 mg/mL). The solution is then cooled to 30° C., seeded and cooled slowly to 20 ° C. After seedbed is formed, water (8.69 L) is added over 1 h. The mixture is aged one hour, then filtered, rinsing with 2:1 water/n-propanol. The solid is dried under vacuum at 40° C. to yield (2R-cis)-2-[[1-[3,5-bis(trifluoro-methyl)phenyl]ethenyl]oxy]-3-(4-fluorophenyl)-4-(phenylmethyl)-mopholine.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the conversion of a starting material containing a carbon-oxygen double bond to a corresponding product containing a carbon-carbon double bond which comprises:

reacting the compound with dimethyl titanocene in a reaction mixture which comprises an organic solvent and a sterically hindered ester, whereby the carbon-oxygen double is replaced by a carbon-carbon double bond to provide an olefin.

2. The process of claim 1 wherein the starting compound containing a carbon-oxygen double bond is selected from the group consisting of aldehydes, ketones, esters, lactones, amides and lactams.

3. The process of claim 1 which further comprises recovery of the product olefin from the reaction mixture.

4. The process of claim 1 which further comprises reacting of the product olefin in situ prior to recovery from the reaction mixture.

5. The process of claim 1 wherein the reaction mixture further comprises titanocene dichloride.

6. The process of claim I wherein the reaction mixture further comprises chloromethyl titanocene.

7. The process of claim I wherein the sterically hindered ester is selected from the group consisting of: t-butyl acetate; 1,1-dimethyl-2-phenylethyl acetate; 1,1-dimethyl-3-phenylpropyl acetate; dihydroterpinyl acetate; isopropyl cyclohexane carboxylate; isopropyl isobutyrate; methyl pivalate; and isobutyl acetate.

8. The process of claim 1 wherein the sterically hindered ester is selected from the group consisting of: 1,1-dimethyl-2-phenylethyl acetate; and t-butyl acetate.

9. The process of claim 1 wherein the sterically hindered ester is 1,1-dimethyl-2-phenylethyl acetate.

10. The process of claim 8 wherein the reaction mixture further comprises titanocene dichloride.

11. The process of claim 8 wherein the reaction mixture further comprises chloromethyl titanocene.

12. The process of claim 1 wherein the organic solvent comprises a solvent which is selected from: tetrahydrofuran; toluene; and mixtures thereof.

13. A process for the preparation of (2R-cis)-2-[[1-[3,5-bis(trifluoromethyl)phenyl]ethenyl]oxy]-3-(4-fluorophenyl)-4-(phenylmethyl)mopholine which comprises:

reacting (2R-cis)-3,5-bis(trifluoromethyl)-benzeneacetic acid 3-(4-fluorophenyl)-4-(phenylmethyl)-2-morpholinyl ester with dimethyl titanocene in a reaction mixture which comprises an organic solvent and a sterically hindered ester.

14. The process of claim 13 wherein the reaction mixture further comprises titanocene dichloride.

15. The process of claim 13 wherein the reaction mixture further comprises chloromethyl titanocene.

16. The process of claim 13 wherein the sterically hindered ester is selected from the group consisting of: 1,1-dimethyl-2-phenylethyl acetate; and t-butyl acetate.

17. The process of claim 16 wherein the organic solvent comprises a solvent which is selected from: tetrahydrofuran; toluene; and mixtures thereof.

18. The process of claim 17 wherein the temperature of the reaction is about 80° C.

* * * * *